(12) United States Patent
Sun

(10) Patent No.: US 9,005,257 B2
(45) Date of Patent: Apr. 14, 2015

(54) UNIVERSAL LOCKING AND COMPRESSION DEVICE FOR BONE PLATE

(76) Inventor: Dexiu Sun, Weifang (CN)

( * ) Notice: Subject to any disclaimer, the term of this patent is extended or adjusted under 35 U.S.C. 154(b) by 154 days.

(21) Appl. No.: 13/641,774

(22) PCT Filed: Jun. 1, 2011

(86) PCT No.: PCT/CN2011/075103
§ 371 (c)(1),
(2), (4) Date: Oct. 17, 2012

(87) PCT Pub. No.: WO2012/068855
PCT Pub. Date: May 31, 2012

(65) Prior Publication Data
US 2013/0041413 A1    Feb. 14, 2013

(30) Foreign Application Priority Data
Nov. 28, 2010   (CN) .......................... 2010 1 0581280

(51) Int. Cl.
A61B 17/80 (2006.01)
(52) U.S. Cl.
CPC .................................. A61B 17/8047 (2013.01)
(58) Field of Classification Search
USPC ............. 606/70–71, 280–282, 286–289, 291, 606/293
See application file for complete search history.

(56) References Cited

U.S. PATENT DOCUMENTS

| 7,776,038 | B2 | 8/2010 | Prien | |
| 2006/0064096 | A1 | 3/2006 | Prien | |
| 2009/0012571 | A1* | 1/2009 | Perrow et al. | 606/280 |
| 2010/0063505 | A1 | 3/2010 | Frigg et al. | |
| 2012/0191138 | A1* | 7/2012 | Kiester | 606/281 |
| 2013/0165980 | A1* | 6/2013 | Cook et al. | 606/286 |

FOREIGN PATENT DOCUMENTS

| CN | 2557090 | 6/2003 |
| CN | 2812855 | 9/2006 |
| CN | 201595922 | 10/2010 |

(Continued)

OTHER PUBLICATIONS

Machine Translation of PCT/CN2011/075103, Dexiu Sun, "Universal Locking and Compression Device for Bone Plate," Retrieved on May 13, 2014.*

(Continued)

*Primary Examiner* — Nicholas Woodall
*Assistant Examiner* — Larry E Waggle, Jr.
(74) *Attorney, Agent, or Firm* — Nixon & Vanderhye, P.C.

(57) ABSTRACT

A kind of bone plate gimbal lock pressure device. The body of the bone plate (1) has a microscler slippery hole (2), in which there has a locking slider (3); on the slider (3) there is a cone-shaped screw hole (3-3) with a cone-head screw (4) inside. The shapes at two inside sides of the microscler slippery hole (2) cross section are internal arc-shaped, and the shapes of the two sides of the locking slider (3) are correspondingly external arc (3-1); in the middle of the locking slider (3) there is a notch (3-2). The locking slider (3) can slide in the microscler slippery hole (2) to meet the pressure requirement, and also can sway from side to side to adjust the direction of the cone-head screw (4) according to the requirement. The two sides of the locking slider (3) are arc; after tightening the screw (4), the arc contact will make the locking slider (3) not take off.

5 Claims, 3 Drawing Sheets

(56) References Cited

FOREIGN PATENT DOCUMENTS

| CN | 101999927 | 4/2011 | | |
|---|---|---|---|---|
| EP | 1654993 | 5/2006 | | |
| FR | 2726461 A1 * | 5/1996 | ............. | A61B 17/80 |
| WO | WO 2008/113191 | 9/2008 | | |
| WO | WO 2011056000 A2 * | 5/2011 | ............. | A61B 17/58 |

OTHER PUBLICATIONS

International Search Report for PCT/CN2011/075103 mailed Sep. 8, 2011.

* cited by examiner

UNIVERSAL LOCKING AND COMPRESSION DEVICE FOR BONE PLATE

This application is the U.S. national phase of International Application No. PCT/CN2011/075103 filed 1 Jun. 2011 which designated the U.S. and claims priority to CN 201010581280.1 filed 28 Nov. 2010, the entire contents of each of which are hereby incorporated by reference.

TECHNICAL FIELD

This invention refers to a kind of bone plate; concretely speaking, it is a lock pressure device of the bone plate.

BACKGROUND TECHNOLOGY

The Bone Plate is currently the most frequently-used internal fixation device for the treatment of bone fracture. As for the traditional metal bone plate, there sets a screw mounting hole on the body of the bone plate, fixed by a screw with cone-shape external screw thread. In order to improve the treatment effect and accelerate the concrescence of the broken ends of fractured bone, there appear some pressure bone plates with the patent number of 200520009461.1 and so on in recent years which realize the pressure by the inclined surface of the screw hole and the screw; They are of short adjustable distance and bad pressure effect, as well as unadjustable direction of the screw, leading to inconvenient operation and influencing the surgery quality. While the gimbal lock metal bone plate with the patent number of 201020014496.5 invented by the applicant can adjust the direction of the screw, but without pressure effect.

Invention Content

This invention aims to provide a kind of bone plate lock pressure device which can adjust not only the screw direction conveniently, but also the pressure distance arbitrarily, against the shortages of the current technology mentioned above, to reduce the difficulty of the operation and improve the treatment effect.

This invention is the improvement of the current bone plates; it sets an elongate slide hole, in which there is a locking slider; on the slider there sets a cone-shaped screw hole where has a cone-head screw. The two sides of the elongate slide hole are intrados, that is, the shapes of the contour line at the two inside sides of the hole's cross section are arc-shaped and the shapes of the two sides of the locking slider are correspondingly external arc; in the middle of the locking slider there is a notch which divides the locking slider into two symmetrical sections connected at the undersurface.

The locking slider can slide in the elongate slide hole, with the adjustable pressure distance so that the pressure effect is quite good. As the two sides of the slider are arc, and the shapes of the two sides of the locking slider are correspondingly external arc either so that the arc contact will make the locking slider not take off after tightening the screw. And the locking slider can move from side to side when operating to adjust the direction of the cone-head screw according to the clinical requirement so as to reduce the operating difficulty and improve the operation quality.

Figure 1:
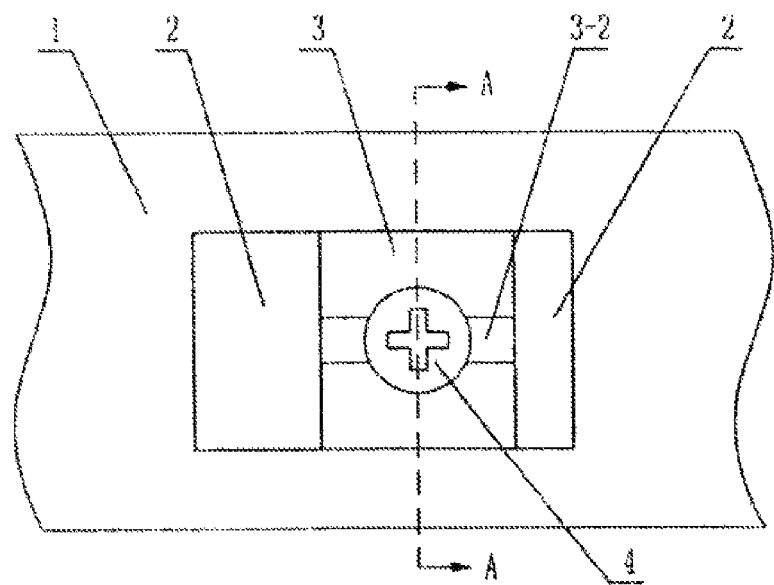
FIG. 1 is the front view of this invention.
Figure 2:
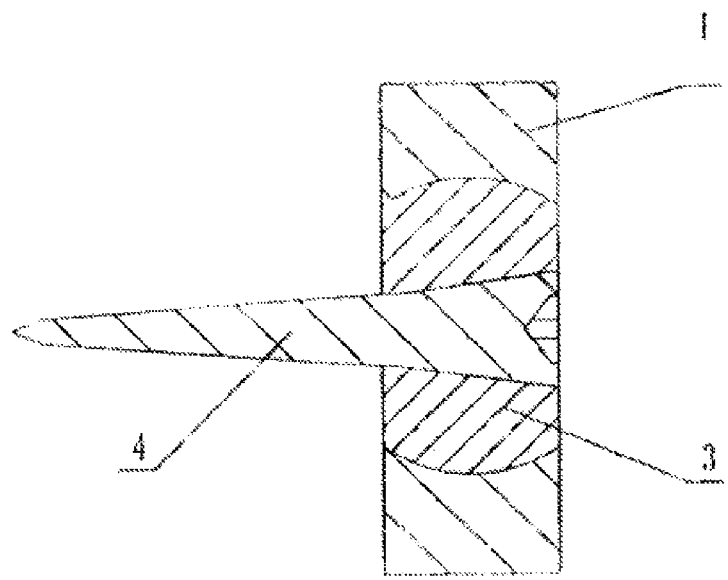
FIG. 2 is A-A section enlarged view in FIG. 1.
Figure 3:
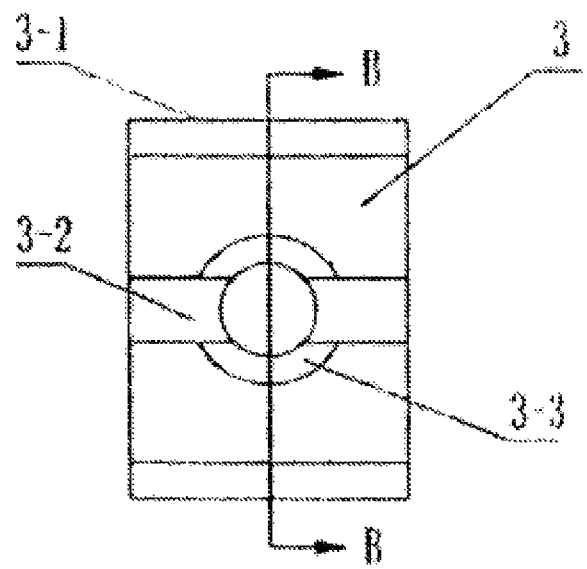
FIG. 3 is the front view of the locking slider.
Figure 4:
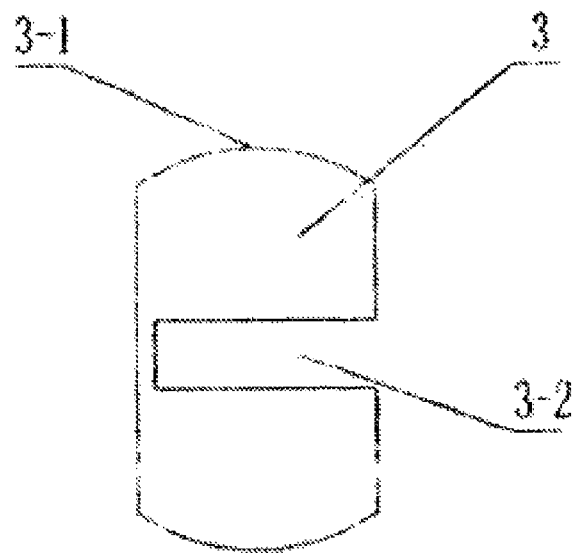
FIG. 4 is left view of FIG. 3.
Figure 5:
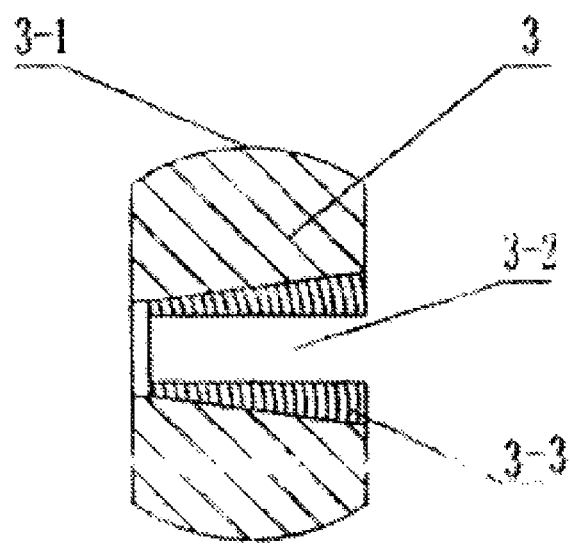
FIG. 5 is B-B section view in FIG. 3.

SPECIFIC IMPLEMENTATION METHOD in this invention, the body of the bone plate (1) has a elongate slide hole (2), in which there has a locking slider (3); on the slider (3) there is a cone-shaped screw hole (3-3) with a cone-head screw (4) inside. the shapes of the contour line at the two inside sides of the elongate slide hole's (2) cross section are arc-shaped, that is, the longitudinal surface of the two sides of the elongate slide hole's (2) is intrados while that of the locking slider (3) is external arc (3-1) correspondingly. In the middle of the locking slider (3) there is a notch (3-2) which divides the locking slider (3) into two sections connected at the undersurface so as to facilitate to lock the locking slider (3) in the elongate slide hole (2) by compressing the two sections inwards when installing. When operating, the locking slider (3) can slide in the elongate slide hole (2) to meet the pressure requirement, and also can sway from side to side to adjust the direction of the cone-head screw (4) according to the clinical requirement. After being adjusted properly, tighten the screw (4) with the two sections of the locking slider (3) opened by the cone head of the cone-head screw, and compressed tightly the inner wall of the elongate slide hole (2) to achieve the lockout. As both are contacted with the cambered surface, it will not be taken off.

The invention claimed is:

1. A bone plate gimbal lock pressure device, comprising: a body of the bone plate having an elongate slide hole, in which there is a locking slider, on the slider there is a cone-shaped screw hole with a cone-head screw inside, wherein: two sides of the elongate slide hole are arc-shaped and concave, and corresponding two sides of the locking slider are correspondingly arc-shaped and convex such that the locking slider is configured to slide and rotate within the elongate slide about an axis of the elongate slide hole; and in the middle of the locking slider there is a notch.

2. A bone plate gimbal lock pressure device according to claim 1, wherein said notch divides the locking slider into two symmetrical sections joined opposite an opening of the notch.

3. A bone plate gimbal lock pressure device according to claim 2, wherein the locking slider is dimensioned such that when the cone-head screw is tightened into the cone-shaped hole each of the two symmetrical sections is compressed against a corresponding side of the elongate slide hole to lock the locking slider into the elongate slide hole.

4. A bone plate gimbal lock pressure device, comprising:
   a body, the body having an elongate slide hole, the elongate slide hole having a longitudinal axis, and the elongate slide hole having opposing surfaces that are concave and arc-shaped;
   a locking slider located within the elongate slide hole, the locking slider having opposing surfaces that are convex and arc-shaped to correspond to respective ones of the opposing surfaces of the elongate slide hole, and the locking slider having a cone-shaped screw hole and a notch positioned between the opposing surfaces of the locking slider; and
   a cone-head screw located in the cone-shaped screw hole, wherein the locking slider is configured to move within the elongate slide hole in a direction parallel to the longitudinal axis of the elongate slide hole and to rotate within the elongate slide hole about the longitudinal axis of the elongate slide hole when the locking slider is not locked in the elongate slide hole.

5. The bone plate gimbal lock pressure device of claim 4, wherein the locking slider is dimensioned such that screwing the cone-head screw into the cone-shaped screw hole forces the opposite surfaces of the locking slider against the opposing surfaces of the elongate slide hole to lock the locking slider in the elongate slide hole.

* * * * *